(12) United States Patent
Keller

(10) Patent No.: US 7,794,595 B2
(45) Date of Patent: Sep. 14, 2010

(54) METHOD FOR ENCAPSULATION, REMEDIATION AND RECOVERY OF SPILLED OIL

(76) Inventor: Brian Charles Keller, 5058 Nortonville Way, Antioch, CA (US) 94531

( * ) Notice: Subject to any disclaimer, the term of this patent is extended or adjusted under 35 U.S.C. 154(b) by 479 days.

(21) Appl. No.: 11/825,940

(22) Filed: Jul. 10, 2007

(65) Prior Publication Data

US 2008/0249348 A1 Oct. 9, 2008

Related U.S. Application Data

(60) Provisional application No. 60/840,789, filed on Aug. 28, 2006.

(51) Int. Cl.
*C02F 1/68* (2006.01)

(52) U.S. Cl. ........................ 210/600; 210/749; 210/767; 210/925

(58) Field of Classification Search ................. 210/600, 210/749, 767, 610–611, 925
See application file for complete search history.

(56) References Cited

U.S. PATENT DOCUMENTS

| 4,886,519 | A | 12/1989 | Hayes et al. |
| 5,401,413 | A * | 3/1995 | Gatt et al. .................... 210/610 |
| 5,756,357 | A | 5/1998 | Wright et al. |
| 6,958,160 | B1 * | 10/2005 | Keller et al. ................ 424/450 |
| 2004/0062780 | A1 | 4/2004 | Keller |
| 2004/0175407 | A1 | 9/2004 | McDaniel |
| 2006/0053791 | A1 | 3/2006 | Prentice, III |

* cited by examiner

*Primary Examiner*—Chester T Barry
(74) *Attorney, Agent, or Firm*—Lee Pederson

(57) ABSTRACT

Diacylglycerol PEGs (DAG-PEGs) are used remediate oil contaminations. DA-PEGs encapsulate the oil into lipsomes in an aqueous environment. The lipsomes sequester the oil from causing damage.

6 Claims, 1 Drawing Sheet

_US 7,794,595 B2_

METHOD FOR ENCAPSULATION, REMEDIATION AND RECOVERY OF SPILLED OIL

RELATED APPLICATIONS

This application claims priority based on U.S. Provisional Patent Application Ser. No. 60/840,789 entitled "Nanotechnology for spilled oil encapsulation, remediation and recovery" filed Aug. 28, 2006.

FIELD OF THE INVENTION

This invention relates to cleaning oil contaminations and to extracting hydrocarbons from oil sands.

BACKGROUND OF THE INVENTION

Part A: Oil Contamination

The environmental and health effects of the average 3,000 oil spills annually worldwide have untoward consequences. An environmentally friendly solution to clean up these spills could have tremendous value to both the geographic region and the biological habitat where the spill occurs. A non-toxic, nano-scale solution to cleaning up petroleum spills both on land and in water is described.

Part B: Extraction of Hydrocarbons from Oil Sands

Oils sands contain a large amount of the world's potential oil reserves. Oil-sand, also called tar sand, is an earthy, dark gray substance with a shiny finish found in various size clumps or clods with a characteristic tar and oil odor. At the same time, it is both greasy and grainy to the touch. It is comprised of sand, clay, bitumen and a small amount of water. Tar sands are mined to extract the hydrocarbon-rich bitumen, which is then converted into synthetic crude oil or refined directly into petroleum products, like gasoline, heating oil, fuel oil and heating oil. Bitumen is a viscous semisolid that can be refined into synthetic crude oil. However, in the Northern Canadian oil sand fields it is trapped in the sand and clay and does not flow at ambient ground temperatures, all of which makes it difficult and expensive to extract. Even in warmer climates, bitumen is difficult to extract from oil sands.

Methods of extracting the bitumen currently use hot water combined with skimming techniques and organic solvents. The process is about 85% efficient when used in surface mining and 60-65% efficient with in-situ, or underground, mining. The current methods result in high fuel consumption and high carbon dioxide emissions. The need for an economical, energy efficient way to extract bitumen from sand without creating excess green house gasses is critical.

BRIEF DESCRIPTION OF THE INVENTION

Oil contaminations are remediated by applying PEG lipids. The PEG lipids encapsulate the oil into liposomes.

DETAILED DESCRIPTION OF PREFERRED EMBODIMENTS

Figure 1:
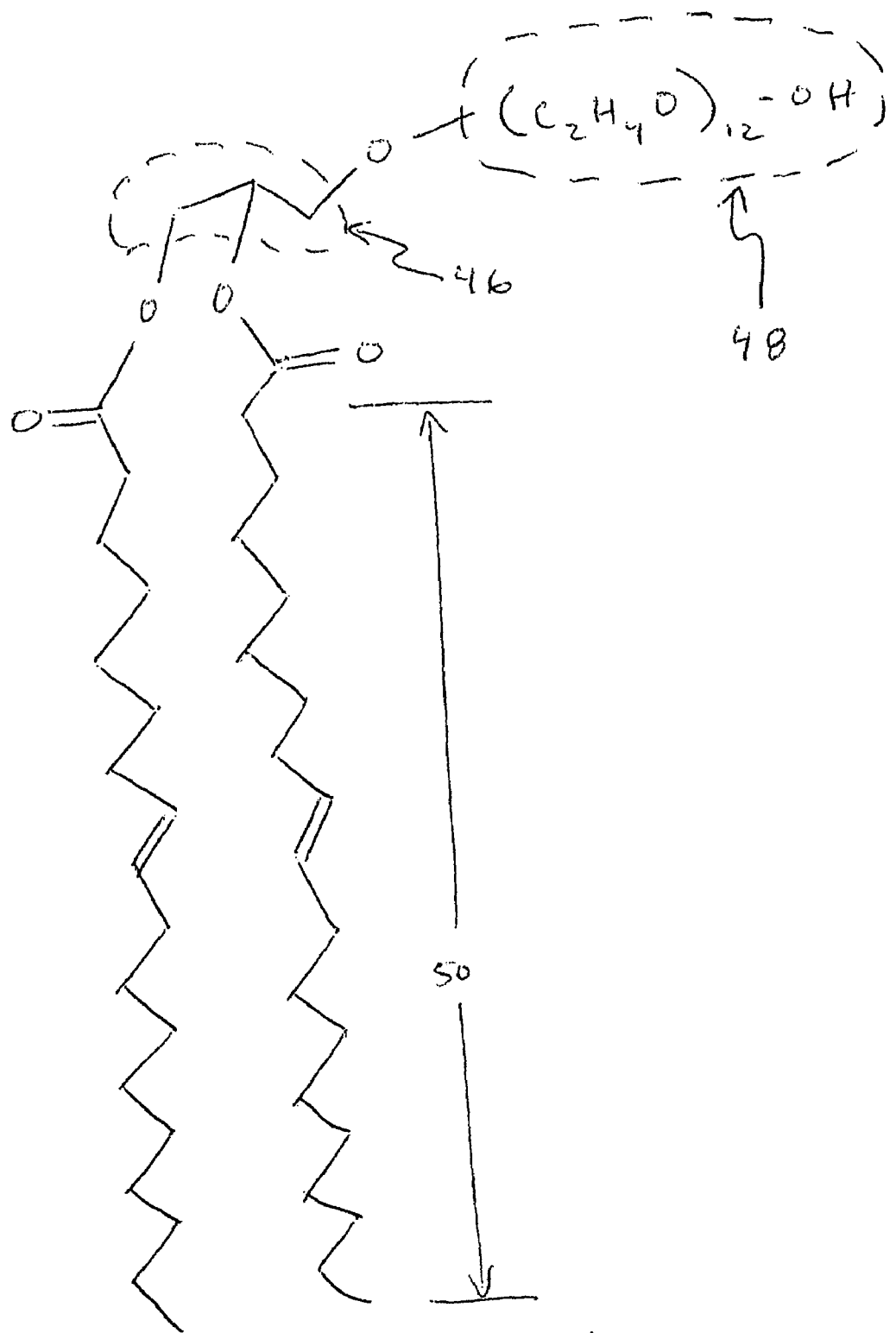
FIG. 1 shows a chemical structure of PEG-12 Glycerol Dioleate

PEG lipid conjugates have been found to possess useful properties for dealing with oil products. Several compositions and methods are described herein.

Part A: Cleaning Oil Contaminations

When certain diacylglycerol-polyethyleneglycol (DAG-PEG) lipids are added to the surface of an oil spill in water, the lipids will entrap both water and oil from the immediate surroundings and disperse the contents and vesicles into a suspension. The DAG-PEG will immediately and spontaneously begin to entrap water and available oil from the spill into thermodynamically stable vesicles. Mechanical mixing via pumping or injecting can help speed the reaction of vesicle formation and encapsulation.

If an oil contamination is on a dry or hydrophobic surface, water must be added to begin the process of vesiculation and oil entrapment. A ratio of about 30:4:1 (water:DAG-PEG:oil) is sufficient for oil encapsulation. If the oil contamination is on an animal, such as a bird or mammal, again water must be added to begin the process of vesiculation and oil entrapment.

Once the oil has been entrapped into vesicles it will remain inside the bi-layers of the vesicle and in suspension indefinitely, allowing for easy clean-up either by washing with more water or with vacuum equipment. The resulting liposome suspension is water washable and can be cleaned off animals, including bird feathers, fur and scales. Additionally, the suspension can be broken and components separated using various techniques. Because these formed vesicles are thermodynamically stable, they will remain as vesicles until disrupted by high energy mechanical shear, by enzyme activity or by heat In the field, the DAG-PEG may be re-used. After treatment of an oil contamination with lipid, a lipid/oil suspension forms. If this suspension is collected, the lipid may be separated from the suspension and reapplied to the contamination. This may be accomplished by optionally heating the suspension and then mechanically separating lipid from the other components by centrifugation or other means.

The invention is useful for cleaning oil contaminations, including but not limited to oil spills in water, oil spills on land, oil contaminations on machinery, and oil contaminations on animals. The invention is useful on crude oil, refined oil, and used oil.

DAG-PEGs are non-toxic and have an $LD_{50}$ of >5 grams/kg, making them suitable for cleaning environmentally sensitive areas and living animals. See e.g., AAPS PharmSci 2004; 6 (2) Article 14.

FIG. 1 shows the chemical structure of PEG-12 Glycerol Dioleate ("PEG-12 GDO"), which includes a glycerol backbone 46, a PEG chain 48, and a tail group 50 having two hydrocarbon chains. Together, the backbone 46 and the PEG chain 48 comprise the head group of the molecule.

PEG-12 GDO and similar lipids are described in co-owned U.S. Pat. No. 6,610,322 entitled "Self-forming, thermodynamically stable liposomes and their applications", which is hereby incorporated by reference.

PEG-12 GDO and PEG-12 GDM (glycerol dimyristate) are among preferred lipids for practicing this invention for two main reasons. First, they are both fluid at 25 degrees C. This allows for easy application to and mixing with an oil contamination. The low melting temperature also allows for easy recovery and recycling of the lipid from oil/DAG-PEG suspensions. Second, these preferred lipids both have packing parameters that allow them to spontaneously form thermodynamically stable liposomes in aqueous solutions, thereby entrapping the oil.

Those skilled in the art will appreciate that DAG-PEGs may be made to have varying lengths of PEG and varying lipid chains. Also, both the PEG and lipid chains may be joined to the backbone using different chemical linkages than shown in FIG. 1. However, any DAG-PEG that is fluid at 25 degrees C. and having proper packing parameters is meant to fall under the scope of this invention.

Without being bound to a theory, it is currently believed that the oil/DAG-PEG suspensions are true liposomes with an enclosed aqueous space and with the oil entrapped in the bilayer.

DAG-PEGs may be useful in treating oil contamination even when the water:lipid oil ratio is less than 30:4:1. Lipid added to oil without water results in the formation of a gel. In some cases, the formation of such gels might be preferable to leaving a contamination untreated or treatment with other methods.

The invention works with many kinds of oil, including crude oil and its various fractions and lubricant oils having paraffin.

In one aspect the invention is a liposome comprising oil and a diacylglycerol-PEG lipid having a melting temperature below about 25 degrees C. The diacylglycerol-PEG lipid preferably has a melting temperature below about 15 degrees C. The weight ratio of diacylglycerol-PEG:oil is preferably greater than about 1:1, and preferably greater than about 4:1. The diacylglycerol-PEG lipid preferably is selected from the group consisting PEG-12 GDO and PEG-12 GDM.

In another aspect the invention is a method of treating an oil contamination comprising applying a DAG-PEG lipid to the contamination. The method may further comprise applying water to the lipid and oil. The lipid preferably has a melting temperature below about 25 degrees C. The weight ratio of diacylglycerol-PEG:oil is preferably greater than about 1:1, and more preferably greater than about 4:1. The diacylglycerol-PEG lipid is preferably selected from the group consisting PEG-12 GDO and PEG-12 GDM. The method may further comprise mechanically mixing the DAG-PEG lipid with the contamination to form a lipid/oil suspension, collecting the resulting lipid/oil suspension, and separating the DAG-PEG lipid from the lipid/oil suspension.

In some cases, mixtures of diacyl-PEG lipids may be useful for solubilizing and/or sequestering oil without the production of liposomes. In other cases, a portion of the lipid/oil suspension may be liposomes and another portion may be particles and structures other than liposomes. This may be due to the DAG-PEG:oil ratio; packing parameters of the lipid; or the composition of the oil. In these cases the invention is a composition comprising oil, water, and a diacylglycerol-PEG lipid having a melting temperature below about 25 degrees C. The diacylglycerol-PEG lipid preferably has a melting temperature below about 15 degrees C. The weight ratio of diacylglycerol-PEG:oil is preferably greater than about 1:1, and more preferably greater than about 4:1. The diacylglycerol-PEG lipid may be selected from the group consisting PEG-12 GDO and PEG-12 GDM.

Some monoacyl PEG lipids are also useful for cleaning oil contaminations. The resulting lipid/oil suspension may include liposomes and/or other particles and structures. Mixtures of acyl-PEG lipids may be useful for solubilizing and/or sequestering oil without the production of liposomes. In these cases the invention is a composition comprising oil, water, and a monoacyl-PEG lipid having a melting temperature below about 25 degrees C. The monoacyl-PEG lipid preferably has a melting temperature below about 15 degrees C. The weight ratio of monoacyl-PEG:oil is preferably greater than about 1:1, and more preferably greater than about 4:1. The monoacyl-PEG lipid may be selected from the group consisting of PEG-8 oleate and PEG-23 oleate.

In another aspect the invention is a method of treating an oil contamination comprising applying a monoacyl-PEG lipid to the contamination. The method further comprises applying water to the lipid and oil. The lipid preferably has a melting temperature below about 25 degrees C., and more preferably below about 15 degrees C. The weight ratio of monoacyl-PEG:oil is preferably greater than about 1:1, and more preferably greater than about 4:1. The monoacyl-PEG lipid may be selected from the group consisting of PEG-8 oleate and PEG-23 oleate. The method may further comprise mechanically mixing the acyl-PEG lipid with the contamination to form a lipid/oil suspension. The method may further comprise collecting the resulting lipid/oil suspension and separating the acyl-PEG lipid from the lipid/oil suspension.

Even though a PEG lipid does not form a liposome in conjunction with oil, the methods described above may still be useful for solubilizing or sequestering oil.

Part B: Extraction of Hydrocarbons from Oil Sands

PEG lipids dissolve the bitumen out of oil sand resulting in a flowable mixture or solution. The flowable form is a medium body, black, shiny liquid that is eminently transportable for refining anywhere in the world via any mechanism or method conceivable. In particular, this flowable form may be transported via pipeline without diluent. Certain PEG lipids provide an even further advantage in that, if the mixture is spilled or leaked it is easily cleaned up because if added to water it immediately gets encapsulated in to vesicles and can be dispersed. It's safer oil. Once at the refinery the PEG lipid can easily be separated from the other hydrocarbons and a barrel would yield normal quantities of gasoline, fuel oil, lubricant oils, heating oils etc and PEG lipid for re-use in the oil sand fields.

The inventor has found a way to extract a high percentage of bitumen from oil-sands using a novel method. In one aspect, the method uses a diacylglycerol-polyethyleneglycol (DAG-PEG) lipid to extract the bitumen. In the initial step 1:1 ratios (v/wt) of DAG-PEG and oil-sand are combined and mixed. It is helpful that the mixing is vigorous enough to break down the small clumps of sand, bitumen and clay. Since no heating is necessary, very little energy is used during this phase. However, heat maybe used to expedite the process. As mixing continues, the lipid and bitumen combine and a black, shiny liquid emerges. This lipid has the characteristics of crude oil in viscosity, appearance and odor. Once the fines and solids (mostly sand) have settled, the liquid fraction can be collected and easily transported to any destination for further extraction or refinement. This immediately makes bitumen less sticky and transportable, without much energy added.

The invention may substantially reduce carbon emissions produced during the production of oil from coal sands. Current methods require heating large amounts of water to high temperature. Such heating is expensive, both in terms of fuel costs and greenhouse gas emissions. Since the PEG lipid is a liquid at ambient temperatures and converts bitumen into a flowable form on contact, it is possible to extract hydrocarbons without thermal input. Our estimate is that this new method will only take 38 kg of $CO_2$ equivalents per barrel of oil extracted compared to the current 85.5 kg $CO_2$ equivalents per barrel.

An additional advantage of the invention is that the flowable PEG lipid-bitumen combination is more easily transportable than bitumen extracted by current means.

After a single extraction, some bitumen remains with the clay and sand fractions. Additional hydrocarbons may be extracted by further PEG lipid treatment. Such treatment may be done in steps or continuously.

As a final step, the addition of ambient temperature water to the mixture of liquid will wash the sand and clay of remaining PEG lipid and most of the bitumen. As water is added the PEG lipid forms nano-sized vesicles. As the vesicles form they encapsulate the lipid soluble bitumen in the interior of the vesicles and remove the bitumen from the pores of the sand particles. The vesicle/water/bitumen fraction is pumped to a processing station to distill off the water.

Mixing and/or heating enhance the rate of conversion of hydrocarbons into a flowable form. In practice, heating may be most advantageous during in situ mining, and mixing may be most advantageous when the oil sands are excavated and the extraction process is performed above ground. The mixing may include grinding the oil sand into particles to provide more surface area for the oil sand to interact with the extraction polymer.

The method is useful when the oil sands have been extracted to an above ground location. A particular advantage of above ground extraction is that the oil sand is more easily ground into particles, preferably fine particles.

This method can also be used for the in situ reserve extraction of bitumen from sand. Challenges facing current in situ process are efficient recoveries, management of water used to make steam, and co-generation of all (otherwise waste) heat sources to minimize energy costs.

The in situ process consists of pumping a PEG lipids into the in situ reserves both horizontally and vertically, similar to the steam extraction patterns currently used. Once the DAG-PEG has been pumped into the oil-sand store site below the surface a production well pump can easily pump the DAG-PEG-bitumen liquid and it can be transported to the refining site. Heating the DAG-PEG to about 35 degrees C. prior to pumping it in situ is helpful in obtaining higher bitumen recovery. Repeating this process 2-4 times will increase yields.

The last phase of in situ mining is to pump ambient temperature water through the same system that the DAG-PEG lipid was introduced and removed. This will cause the DAG-PEG to form vesicles and remove some of the remaining bitumen.

Once the water/lipid/bitumen has been removed from the ground the vesicles can be broken with heat of about 50 degrees C. and the water can be distilled off and the resultant lipid-bitumen mixture can be shipped to a refining facility.

One advantage to the lipid-bitumen combination is that it is environmentally friendly. If this liquid is spilled into water nano-vesicles spontaneously and immediately form around the lipid soluble bitumen and disperse into the water column. The nano-vesicles are stable, non-toxic and eco-friendly. If it leaks out of a pipeline and onto the ground it can easily be cleaned up with water.

In one aspect the invention is a method of extracting hydrocarbons from oil sand, the method comprising locating the oil sand, providing a diacyl-PEG polymer in contact with the oil sand, allowing the polymer to convert the hydrocarbons in the oil sand into a flowable form, and collecting the flowable form. The method may further comprise separating the diacyl-PEG polymer from the hydrocarbons. The diacyl-PEG polymer may comprise a glycerol backbone The diacyl-PEG polymer preferably has a melting temperature below about 25 degrees C., and more preferably below about 15 degrees C. The diacyl-PEG polymer may be selected from the group consisting of GDO-12, GDO-23 and GDL-23. The location of the oil sand may be underground or above ground. The method may further comprise preheating the diacyl-PEG polymer and/or grinding the oil sand into particles.

The invention is also a method of converting hydrocarbons from oil sand into a flowable farm comprising locating the oil sand and providing a diacyl-PEG polymer in contact with the oil sand. The diacyl-PEG polymer comprises a glycerol backbone. The diacyl-PEG polymer preferably has a melting temperature below about 25 degrees C., and more preferably below about 15 degrees C. The diacyl-PEG polymer may be selected from the group consisting of GDO-12, GDO-23 and GDL-23. The location of the oil sand may be underground or above ground. The method may further comprise preheating the diacyl-PEG polymer and/or grinding the oil sand into particles.

The invention is also a method of extracting hydrocarbons from oil sand (tar sand) comprising locating the oil sand, providing an acyl-PEG polymer in contact with the oil sand, allowing the polymer to convert the hydrocarbons in the oil sand into a flowable form; and collecting the flowable form. The method may further comprise separating the acyl-PEG polymer from the hydrocarbons. The acyl-PEG polymer preferably has a melting temperature below about 25 degrees C., and more preferably below about 15 degrees C. The acyl-PEG polymer may be selected from the group consisting of PEG-23 oleate and PEG-8 oleate. The location of the oil sand may be underground or above ground. The method may further comprise preheating the diacyl-PEG polymer and/or grinding the oil sand into particles.

During the process of extracting hydrocarbons from oil sands, useful compositions may be produced. Therefore, the invention also includes a composition comprising oil sand and a diacyl or acyl-PEG polymer in contact with the oil sand. The composition further comprises a flowable form of hydrocarbons from the oil sand solubilized by the polymer.

The methods described for diacyl-PEG lipids may be similarly useful for certain monoacyl-PEG lipids. Unsaturated lipids conjugated to relatively short PEG chains (8-23 subunits) are expected to be among the most suitable polymers in this category.

General Considerations

DAG-PEG lipids with low melting points are preferred lipids for both sequestering oil contaminations and extracting hydrocarbons for bitumen. While the exemplary DAG-PEG in FIG. 1 has a glycerol backbone and specific linkages between the backbone, acyl groups and PEG chain, those of skill in the art will realize that similar molecules will also be suitable for practicing the inventions disclosed herein. For example, different chemical linkages and different backbones may be used to construct DAG-PEG lipids.

Similarly, monoacyl-PEG polymers may be constructed with a variety of chemical linkages.

Though polymers with low melting points are preferred, compounds with higher melting points may also be used in practicing certain aspects of the invention. For example, GDO-45, GDM-45 and GDP-23 all have melting temperatures higher than 25 degrees C. However, when heated to a liquid phase these polymers are useful for both sequestering oil contaminations and extracting hydrocarbons for bitumen.

Combinations of polymers are also useful. Since particular polymers may vary slightly in their ability to interact with the various fractions of oil and bitumen, it may sometimes be useful to tailor a combination of PEG-lipid conjugates to a particular application.

In a broad sense, when water is not present the invention is a flowable mixture of PEG-lipid and hydrocarbons/oil. When water is present, the invention is a lipsome comprising PEG-lipid and hydrocarbons/oil.

The invention may be used for hydrocarbon extraction from oil sand by omitting the step of extracting without water. In such a case, the use of water will result in liposomes and/or other structures suspended in an aqueous solution. Such a process may be useful to recover remaining fractions from oil sands previously processed by conventional methods.

When relatively small amounts of DAG-PEGs are added to oil in an aqueous environment liposomes form spontaneously, thereby entrapping some of the oil. Similarly, adding relatively small amounts of PEG lipids to bitumen results in converting hydrocarbons to a flowable form. For better cleaning/extraction, the PEG lipids should be applied in larger amounts and repeatedly, if necessary.

Both flowable hydrocarbon/PEG lipid mixtures and oil/liposome suspensions may require extra separations before extraction, recovery or refining processes can be done. There is typically about 12% water in oil sands. Much of this water will be taken up in the flowable form and must later be removed, as must the water in the liposome suspensions. Also, fine components in bitumen may require gravitational separation such as centrifugation or inclined plate settling.

The compositions and methods described are suitable for extracting hydrocarbons from oil sand, oil shale, tar sand, or any similar deposit.

While preferred embodiments of the present invention have been described, those skilled in the art will recognize that other and further changes and modifications can be made without departing from the spirit of the invention, and all such changes and modifications should be understood to fall within the scope of the invention.

EXAMPLE 1

Entrapment and Dispersion of Oil in Water

HD 30 motor oil was added to water. Then PEG-12 GDO was added in a 1:4 ratio (oil:PEG-12 GDO). An opaque white suspension formed which showed liposomes when examined under a light microscope at 600×. The oil was entrapped and dispersed in the suspension.

EXAMPLE 2

Cleaning an Environmental Oil Spill (Predictive)

A large quantity of medium weight crude oil is spilled from a ruptured tanker and the oil washes onto a coastal area. The water temperature is 45 degrees C. and the air temperature is 50 degrees. The beach is sprayed with diacyl lipid-PEGs to disperse the oil, thereby forming liposomes.

EXAMPLE 3

Recovery of Hydrocarbons from Oil Sand

These experiments were conducted at room temperature, about 22° C.

The objective of this experiment was to test various non-toxic solvents for their ability to release bitumen from Canadian oil-sand.

The goal of this experiment was to find the relative solvent capability of various solvents and compare them to identify the best solvents for the purpose of releasing bitumen from oil-sand at low energy expense and decreased green-house gas release.

Table 1 lists the solvents tested. All solvents were fluids at ambient temperature. A weighed amount of each solvent (between 15 grams and 35 grams) was put into a Pyrex mortar and pestle. An equal amount of Canadian oil-sand was weighed and put into the solvent. The 1:1 mixture was left to stand for 10 minutes then triturated for 2 minutes and left to stand for 10 minutes. Solubility was graded by observation of the color of the .liquid which correlates to the amount of bitumen that has been released from the sand and into the solvent. The darker the liquid, the more bitumen was released. In the second step the resultant liquid was decanted off and more solvent was added to the oil-sand+residual solvent in the mortar. The mixture was allowed to stand for 10 minutes and then triturated for 2 minutes then allowed to stand for 10 more minutes. The resultant liquid was observed for color change, odor and clarity and decanted off. The process was repeated a third time. The resultant decanted liquid, collected during all phases was observed for solubility capacity. Using a scoring scale for solubility from 0-10, where 0 is insoluble and 10 is totally soluble each solvent was scored. (Table 1) The scoring table categorizes the solubity scores into four categories: is=insoluble (0), ss=slightly soluble(1-3), ms=moderately soluble (4-6), s=mostly soluble (7-9) and ts=totally soluble (10).

TABLE 1

Solubility Scores of Various Solvents for Canadian Oil Sand

| Solvent | Melting Temp ° C. | Insoluble | Slightly Soluble | Moderately Soluble | Mostly Soluble | Totally Soluble |
|---|---|---|---|---|---|---|
| Isopropyl alcohol | −88.5 | | 1 | | | |
| Ethyl alcohol | −117.3 | | 1 | | | |
| Benzyl alcohol | −15.19 | | | 4.5 | | |
| Olive oil | −6 | | 0.5 | | | |
| Safflower oil | −16 | 0 | | | | |
| Soybean oil | −16 | 0 | | | | |
| Borage oil | −12 | | 0.5 | | | |
| Castor oil | −18 | 0 | | | | |
| Sesame oil | −14 | 0 | | | | |
| Corn oil | −15 | 0 | | | | |
| Glycerin | 17.8 | 0 | | | | |
| Propylene glycol | −59 | 0 | | | | |
| Butylene glycol | −50 | 0 | | | | |
| Ethoxydiglycol | −35 | | 1 | | | |
| Isopropyl myristate | 3 | | 3 | | | |
| Acetylated lanolin alcohol | 6 | | | 6 | | |
| Isocetyl stearoyl state | 4 | | | | 7 | |
| Lenoleic acid | −12 | | | | 9 | |

TABLE 1-continued

Solubility Scores of Various Solvents for Canadian Oil Sand

| Solvent | Melting Temp ° C. | Insoluble | Slightly Soluble | Moderately Soluble | Mostly Soluble | Totally Soluble |
|---|---|---|---|---|---|---|
| Linolenic acid | −14 | | | | 9 | |
| Oleic acid | −16 | | | | 9 | |
| Caprylic/Capric triglyceride | 5 | | | 6 | | |
| Sorbitan Oleate | | | | | | |
| PEG-8 | 12 | | | | 7 | |
| PEG-4 | 10 | | 1 | | | |
| PEG-12 Glyceryl Dioleate (GDO-12) | 10 | | | | | 10 |
| PEG-12 Glyceryl Dimyristate (GDM-12) | 15 | | | | 9 | |
| PEG-23 Glyceryl Dimyristate (GDM-23) | 16 | | | | 9 | |
| PEG-23 Glyceryl Dilaurate (DGL-23) | 8 | | | | | 10 |
| PEG-23 Glyceryl Dioleate (GDO-23) | 12 | | | | | 10 |

EXAMPLE 4

Recovery of Hydrocarbons from Oil Sand (Predictive)

Additional solvents are tested for their ability to convert bitumen into a flowable form. The experiment is carried out as in Example 3, except that it is done at a temperature of 40 degrees C. The solvents in Table 2 all achieve a solubility score of 9 or 10.

TABLE 2

Various Solvents for Canadian Oil Sand

| Solvent | Melting Temp ° C. |
|---|---|
| PEG-23 Glyceryl Dipalmitate (GDP-23) | 31.2 |
| PEG-45 Glyceryl Dimyristate (GDM-45) | 33.2 |
| PEG-45 Glyceryl Dioleate (GDO-45) | 36.3 |

EXAMPLE 5

Recovery of Hydrocarbons from Oil Sand (Predictive)

PEG-23 oleate is tested for its ability to convert bitumen into a flowable form. The experiment is carried out as in Example 3. The solvent achieves a solubility score of 9 or 10.

The invention claimed is:

1. A method of treating an oil contamination, comprising: applying a DAG-PEG lipid to the oil of said oil contamination.

2. The method of claim 1, further comprising applying water to the lipid and oil.

3. The method of claim 1, where the lipid has a mlting temperature below about 25 degrees C.

4. The method of claim 1, where the weight ratio of diacylglycerol-PEG: oil is greater than about 4:1.

5. The method of claim 1, where the diacylglycerol-PEG lipid is selected from the group consisting of PEG-12 GDO and PEG-12 GDM.

6. The method of claim 1, further comprising:
mechanically mixing the DAG-PEG lipid with the contamination to form a lipid/oil suspension;
collecting the resulting lipid/oil suspension; and
separating the DAG-PEG lipid from the lipid/oil suspension.

* * * * *